(12) United States Patent
Holsti

(10) Patent No.: US 12,079,027 B2
(45) Date of Patent: Sep. 3, 2024

(54) SYNCHRONIZING PHYSIOLOGICAL MEASUREMENT DATA STREAMS

(71) Applicant: Polar Electro Oy, Kempele (FI)

(72) Inventor: Jussi Holsti, Kempele (FI)

(73) Assignee: Polar Electro Oy, Kempele (FI)

( * ) Notice: Subject to any disclaimer, the term of this patent is extended or adjusted under 35 U.S.C. 154(b) by 838 days.

(21) Appl. No.: 17/267,826

(22) PCT Filed: Sep. 9, 2019

(86) PCT No.: PCT/EP2019/073964
§ 371 (c)(1),
(2) Date: Feb. 11, 2021

(87) PCT Pub. No.: WO2020/053133
PCT Pub. Date: Mar. 19, 2020

(65) Prior Publication Data
US 2021/0202061 A1    Jul. 1, 2021

(30) Foreign Application Priority Data
Sep. 10, 2018 (EP) .................................... 18193345

(51) Int. Cl.
*G06F 1/10* (2006.01)
*G06F 3/01* (2006.01)
*G16H 40/67* (2018.01)

(52) U.S. Cl.
CPC ................ *G06F 1/10* (2013.01); *G06F 3/011* (2013.01); *G06F 3/014* (2013.01); *G06F 3/015* (2013.01);

(Continued)

(58) Field of Classification Search
CPC . G06F 1/10; G06F 3/011; G06F 3/014; G06F 3/015; G06F 2203/011; G16H 40/67; H04Q 2209/43
See application file for complete search history.

(56) References Cited

U.S. PATENT DOCUMENTS 10,362,995 B1 * 7/2019 Chen .................. A63B 24/0021
2009/0245279 A1 * 10/2009 Wan .................. H04W 72/1215
370/468

(Continued)

FOREIGN PATENT DOCUMENTS

WO    WO-2018013569 A1 *  1/2018  ........... A61B 5/0022

OTHER PUBLICATIONS

International Search Report and Written Opinion received for PCT Application Serial No. PCT/EP2019/073964 dated Nov. 20, 2019, 11 pages.

(Continued)

*Primary Examiner* — Glenn A. Auve
(74) *Attorney, Agent, or Firm* — FisherBroyles, LLP

(57) ABSTRACT

There is provided a method in a collector device of a physiological performance measurement system, which includes: broadcasting a timing signal on a predetermined radio channel; receiving a data packet from each of a plurality of peripheral devices configured to perform measurements with respect to one or more users and to transmit physiological measurement data on the one or more users to the collector device, wherein the data packet indicates a clock value of the respective peripheral device as a response to the broadcasting the timing signal; and synchronizing data streams from the plurality of peripheral devices with each other based on the indicated clock values. A respective method is described for the peripheral device.

20 Claims, 9 Drawing Sheets

(52) U.S. Cl.
CPC ....... *G16H 40/67* (2018.01); *G06F 2203/011* (2013.01); *H04Q 2209/43* (2013.01)

(56) References Cited

U.S. PATENT DOCUMENTS

| | | |
|---|---|---|
| 2012/0004516 A1 | 1/2012 | Eng et al. |
| 2015/0092642 A1* | 4/2015 | Geboff ................. H04L 69/329 370/350 |
| 2016/0250517 A1* | 9/2016 | Tilvis ...................... H04Q 9/00 700/91 |
| 2017/0296070 A1 | 10/2017 | Wegerich et al. |
| 2017/0359162 A1* | 12/2017 | Granqvist ............... H04W 4/80 |
| 2018/0077530 A1 | 3/2018 | Mueggenborg et al. |
| 2019/0014549 A1* | 1/2019 | Kwan ................. H04W 56/004 |
| 2021/0345270 A1* | 11/2021 | Murali ................... A61B 5/257 |

OTHER PUBLICATIONS

Extended European Search Report received for EP Patent Application Serial No. 18193345.8 dated Mar. 6, 2019, 11 pages.

\* cited by examiner

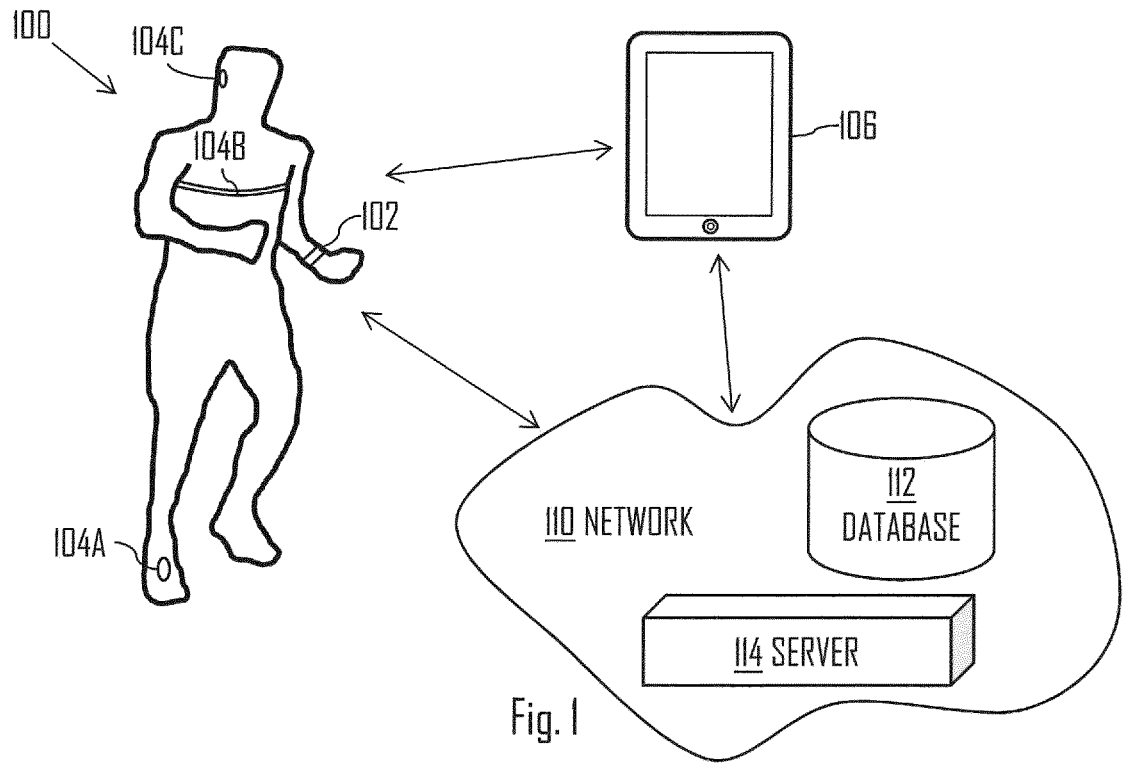
Fig. 1
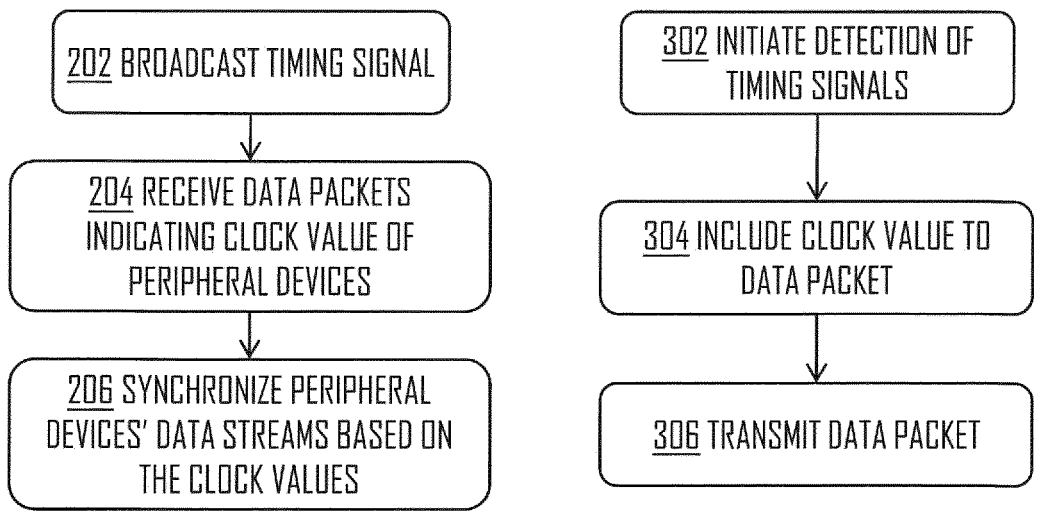
Fig. 2
Fig. 3

SYNCHRONIZING PHYSIOLOGICAL MEASUREMENT DATA STREAMS

CROSS-REFERENCE TO RELATED APPLICATIONS

This application claims benefit and priority to and is a National Phase application of International Application No. PCT/EP2019/073964, filed Sep. 9, 2019, which claims benefit and priority to European Application No. 18193345.8, filed Sep. 10, 2018, which are incorporated by reference herein in their entireties.

FIELD

The invention relates to physiological data measurement. More particularly, the invention relates to synchronizing data streams from a plurality of peripheral devices performing measurements.

SUMMARY

Peripheral devices are used as sensors to measure physiological measurement data of a user or users. It is possible to utilize more than one peripheral device where the peripheral devices transmit measurement data to a collector device, such as a wrist unit or a mobile phone. It may be beneficial to provide new solutions which enhance the way how different data streams from different peripheral devices are synchronized in order to, for example, obtain more accurate metrics that are derivable from combination of the different data streams.

According to an aspect, there is provided the subject matter of the independent claims. Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which FIG. 1 illustrates a system to which embodiments of the invention may be applied;

FIGS. 2 and 3 illustrate flow diagrams according to some embodiments;

DETAILED DESCRIPTION

Figure 4:
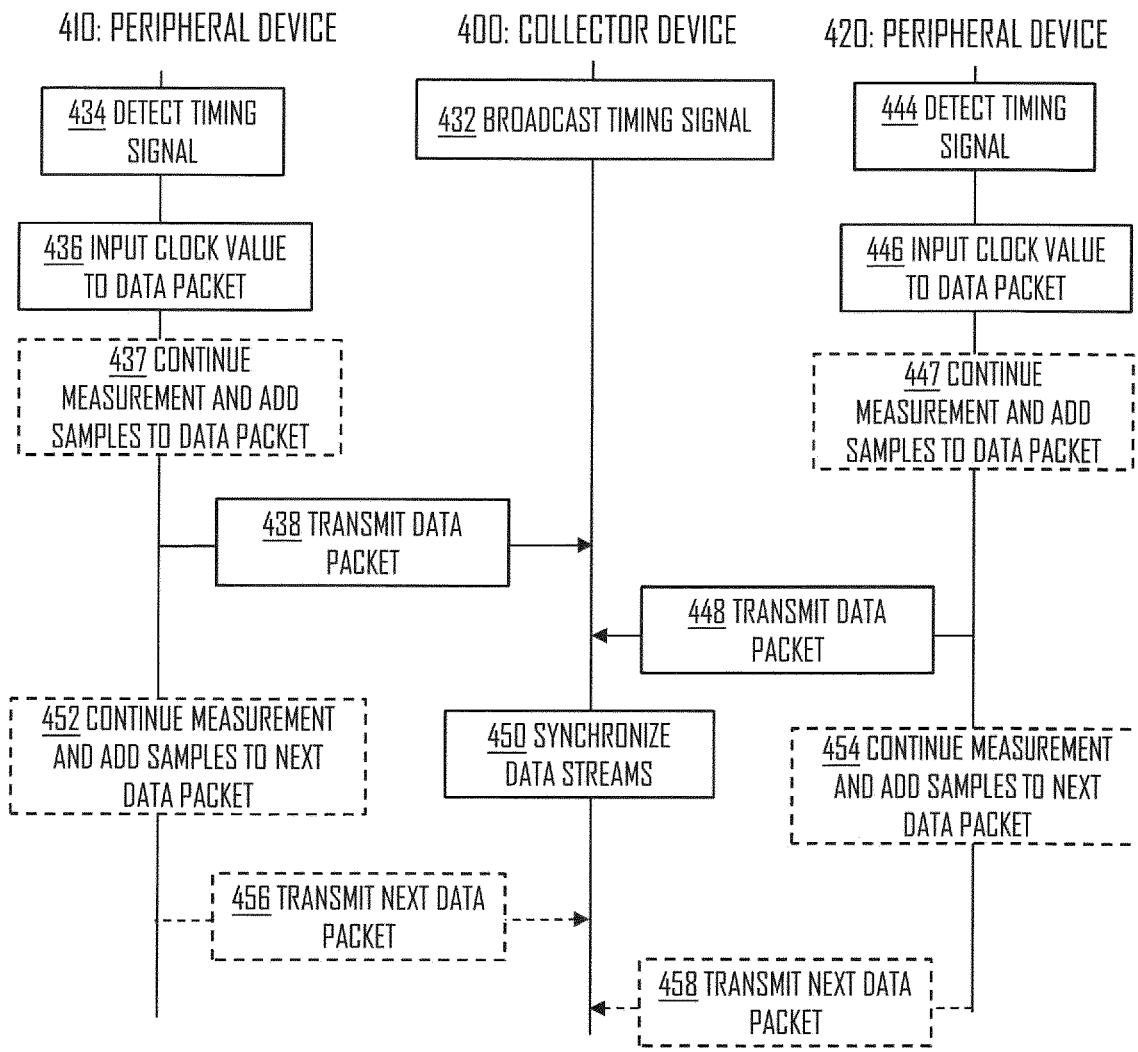
FIG. 4 illustrates a signal diagram according to an embodiment.

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

FIG. 1 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible using one or more devices described with respect to FIG. 1 and in the embodiments below.

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices. I.e. the embodiments are not necessarily limited to wrist device or devices 102.

The wrist device 102 may be, for example, a smart watch, a smart device, sports watch, and/or an activity tracking apparatus (e.g. bracelet, arm band, wrist band, mobile phone). The wrist device 102 may be used to monitor physical activity of the user 100 by using data from internal sensor(s) comprised in the wrist device 102, data from external sensor device(s) 104A-C, and/or data from external services (e.g. training database 112). It may be possible to receive physical activity related information from a network 110, as the network may comprise, for example, physical activity-related information of the user 100 and/or some other user(s). Thus, the wrist device 102 may be used to monitor physical activity related information of the user 100 and/or the other user(s). Naturally, one or more of the external sensor device(s) 104A-C may be worn by the other user(s), and thus information received from said one or more sensor device(s) 104A-C may be monitored from the wrist device 102 by the user 100. The network 110 may comprise the training database 112 and/or the server 114. The server 114 may be configured to enable data transfer between the training database 112 and some external device, such as the wearable device. Hence, the database 112 may be used to store cardiac activity measurement data, for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on a wireless communication protocol, such as Bluetooth® protocol, for example. Other wireless communication methods, such as Wireless Local Area Network (WLAN) and/or Near Field Communication (NFC), may also be used.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating with the cellular network. It is also pointed out that, in general, the wearable device may comprise a communication circuitry capable of cellular, Bluetooth® (e.g. BLE), NFC, WLAN, and/or LAN communication.

The wrist device 102 may be used to monitor activity and/or inactivity of the user 100. Similarly, the portable electronic device 106 may be used to monitor the activity and/or inactivity of the user 100. Such may require the portable electronic device 106 to acquire physical activity-related data from the wrist device 102, some other wearable device, and/or from external sensor device(s) 104A-C. However, it may be that the portable electronic device 106 determines activity and/or inactivity of the user 100 by utilizing internal sensor(s), such as accelerometer or satellite positioning circuitry.

The wrist device 102 may comprise a cardiac activity circuitry configured to determine cardiac activity of the user 100, such as heart rate, Heart Beat Interval (HBI) and/or Heart Rate Variability (HRV), for example. The cardiac activity circuitry may comprise an optical cardiac activity sensor unit configured to measure the cardiac activity of the user 100. Example of such sensor may be a PPG (photoplethysmography) sensor. The optical cardiac activity sensor unit may detect the cardiac activity of the user 100 by optical measurement, which may comprise emitting light towards body tissue of the user 100 and measuring the bounced, reflected, scattered and/or emitted light from the body tissue of the user 100. The emitted light may alter when travelling through veins of the user 100 and the alterations may be detected by the optical cardiac activity sensor unit. By using the detected data, the wrist device 102, may determine cardiac activity of the user 100, such as heart rate for example. The optical cardiac activity sensor unit may obtain via the measurement a cardiac activity signal characterizing or carrying the cardiac activity information on the user. As understood, similar cardiac activity circuitry may be comprised in some other wearable device also.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other wearable device may comprise a processing circuitry configured to obtain the cardiac activity measurement data from the cardiac activity circuitry and to process said data into cardiac activity information, such as a cardiac activity metric characterizing the cardiac activity of the user 100. For example, the measurement data of the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, and/or a polarization blood flow sensor.

In an embodiment, the wearable device comprises a motion circuitry configured to measure motion induced by the user 100 to the wearable device, for example, by moving hand (if the wearable device is the wrist device). The motion circuitry may comprise one or more gyroscopes, one or more accelerometers and/or one or more magnetometers. The motion circuitry may use other motion data, such as location data of the user, to determine motion of the user 100. For example, the motion circuitry may comprise a satellite positioning circuitry, such as a global navigation satellite system (GNSS) circuitry. The GNSS circuitry may comprise, for example, a Global Positioning System (GPS) and/or a GLObal NAvigation Satellite System (GLONASS). The satellite positioning circuitry may be used for receiving satellite positioning data. The satellite positioning data may be used, by the wearable device, to determine motion and/or location of the user 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus for example, the satellite positioning data may also be utilized in the sensor fusion.

It is also noted that wrist device 102 is not always necessary to be used. For example, the portable electronic device (PED) 106 may be used to monitor physical performance and/or exercise of the user 100 or plurality of users (e.g. can be used by a trainer of the plurality of users). The PED 106 may be, for example, a mobile phone, smart phone, tablet computer, cycling computer (can be referred to as a bike computer) and/or any other portable device that can be used to receive physical activity data on user or users directly or indirectly from one or more sensors associated with the user or users, and process said data into one or more performance metrics describing, for example, intensity of the physical exercise. Hence, PED 106 and wrist device 102 may be used in a similar way either alone or in combination with each other to monitor physical performance of the user 100 or users.

As already discussed, the user 100 may use/wear a plurality of different sensors. For example, (s)he may use one sensor (e.g. chest heart rate monitor) to monitor cardiac activity via electrode based measurement and another sensor (e.g. wrist unit sensor, head sensor or arm sensor) to monitor cardiac activity via optical measurement. Both sensors may transmit data to same collector device which can be, for example, the wrist device 102 or the PED 106, or potentially both. Benefits of using more than one sensor to measure similar or same parameter/metrics may be increased robustness of the measurement and/or possibility to measure new metrics which cannot be reliably measured using only one sensor at one location. It is similarly possible to use more than one sensor to measure, for example, motion, power and/or force. It is also possible to use two or more sensors wherein each sensor measures a different parameter or metric. Later it is discussed, via examples, what kind of different parameters may be measured simultaneously to which the provided solution could provide improvements.

Generally, when a sensor measures and transmits data to a collector device there is delay caused by the used transmission protocol. For example, if the sensor transmits data via wireless connection (e.g. Bluetooth®, such as Bluetooth® Smart which can also be referred to as Bluetooth® Low Energy (BLE)) the collector device, there is delay in the transmission caused by said wireless connection. The collector device is unaware of this delay. The amount or delay can potentially be estimated, but it may change between implementations and cases, and therefore the collector device cannot determine the exact moment when the received (i.e. received from the sensor) measurement sample or samples were obtained by the sensor. Utilizing only one sensor such may not be a big of a problem as the delay may remain relatively constant, thus providing reliable physical performance metrics obtained by processing the data. I.e. the delay in the data should only cause delay in displaying the data. A skilled person may understand that e.g. 1 second delay in displaying heart rate may not be of a significant importance. However, if more than one sensor is used, the situation becomes trickier as now the delays (which most probably are different) in data streams received from different sensors may cause problems in obtaining reliable physical performance metrics. Furthermore, if sensors are used to measure performance of different users, the data streams may need to be synchronized in order to obtain comparable and/or combined metrics/parameters between the users. Hence, there seems to be room for providing solutions which enable synchronization of different data streams obtained from different sensors.

FIG. 2 illustrates a flow diagram according to an embodiment. Referring to FIG. 2, a method in a collector device of a performance measurement system (e.g. the system of FIG. 1) is shown, the method comprising: broadcasting (block 202) a timing signal on a predetermined radio channel; receiving (block 204) a data packet from each of a plurality of peripheral devices configured to perform measurements with respect to one or more users and to transmit physiological measurement data on the one or more users to the collector device, wherein the data packet indicates a clock value of the respective peripheral device as a response to the broadcasting the timing signal; and synchronizing (block 206) data streams from the plurality of peripheral devices with each other based on the indicated clock values.

In an embodiment, the data packet comprises a time stamp indicating timing of the physiological measurement data. The time stamp may indicate a timing when the physiological measurement data has been measured by the respective peripheral device that transmitted the data packet. The time stamp may have been measured with a clock of the respective peripheral device, and the same clock may be used to provide the time stamp and the clock value in the data packet. In other words, as the physiological measurement data is generated in the peripheral device, the time stamp at the time of the generation may be recorded and added to the data packet carrying the physiological measurement data. As a consequence, the collector device becomes aware of the actual measurement timing of the physiological measurement data regardless of any processing or transmission delays subsequent to the recording of the time stamp. The time-stamping may be unified across the peripheral devices in the sense that the peripheral devices record the time stamps in a similar manner. For example, peripheral devices configured to detect blood pulse waves may record, as the time stamp, a time instant when the blood pulse is detected. Accordingly, the physiological measurement data can be synchronized by the collector device more accurately.

In an embodiment, the receiving of block 204 is performed as a response to broadcasting the timing signal. Broadcasting may refer to BLE broadcasting for example. In general, broadcasting is a transmission which is directed to multiple receives. Hence, for example, all BLE devices in range may receive the timing signal. However, the BLE devices may employ white list or black list at least in some examples so that only relevant broadcast messages are processed. On the other hand the response received in block 204 may be transmitted based on the broadcasted timing signal, but on scheduled radio resources or scheduled transmission window. That is, it may be that the data packet would be transmitted regardless of the broadcasted timing signal. However, according to the proposed solution, the broadcasted timing signal may cause the receiver device to include its clock value into the next data packet.

FIG. 3 illustrates a flow diagram according to an embodiment. Referring to FIG. 3, a method in a peripheral device of a performance measurement system (e.g. system of FIG. 1) is shown, the method comprising: initiate detection (block 302) of timing signals on a predetermined radio channel, wherein the peripheral device is configured to perform measurements with respect to a user and to transmit physiological measurement data on the user to a collector device; in response to detecting a timing signal broadcasted by the collector device, including (block 304) an information element indicative of a clock value of the peripheral device into a data packet to be transmitted during a transmission window; and transmitting (block 306) the data packet to the collector device during the transmission window.

In an embodiment, the broadcasting is performed according to Bluetooth® (e.g. BLE) standards. Similarly, the data packets may be transmitted and received according to Bluetooth® (e.g. BLE) standards. Peripheral device(s) described with respect to FIGS. 2 and 3 may refer to, for example, sensor devices which are discussed above. Such sensor devices may comprise cardiac activity circuitry, such as electrocardiography (ECG) sensor and/or photoplethysmography (PPG) sensor, pressure sensor, motion circuitry, force sensor, speed sensor, acceleration sensor, satellite positioning circuitry (e.g. GPS) and/or gyroscope (or some other gyro sensing device) to name a few examples. For example, the sensors may refer to sensors 104A-C. For example, the sensor may comprise the above mentioned motion circuitry and/or the cardiac activity circuitry. These sensors may themselves be peripheral devices and/or be comprised in a peripheral device(s). For example, the sensor (s) may be comprised in a chest strap (e.g. ECG sensor, such as electrode based measurement), arm or armband that measures PPG, foot pod (e.g. speed sensor, such as a stride sensor), shoe insole (e.g. force and/or pressure sensor), bike computer, wrist unit (or wrist device) and/or a ski pole. So, it is also possible that the PED 106 and/or the wrist device 102 is a peripheral device in some embodiments. For example, if wrist device 102 is used to measure PPG and chest strap/sensor is used to measure PPG, the collector device may be, for example, the PED 106. In some embodiments, the collector device may be the wrist device 102.

In an embodiment, the broadcasting, e.g. according to Bluetooth® standards, is passive broadcasting. This may mean, for example, that the collector device broadcasts the timing signal (e.g. advertising packet comprising the timing signal or timing value). The peripheral devices may not respond to the broadcasted advertising packet with a scan response, for example. I.e. the peripheral devices may be passive scanners that may receive data from the collector device which may be an advertising device, but do not respond to the advertising packet with a scan response. Instead, the peripheral devices may obtain clock value at the time instant when the advertising packet is received and indicate that clock value in the next data packet of a data stream. The data stream transmission may utilize a device-to-device connection link (i.e. between peripheral device and the collector device). The broadcasting may not utilize said connection link, and therefore the same advertising packet can be detected by each peripheral device.

It is noted that, according to an example embodiment, the transmitted data packets of data streams (e.g. cardiac activity data stream, such as ECG or PPG data streams) may be measured and transmitted in real time by the peripheral devices. Hence, the measurements system may refer to real-time measurement system. It is possible that the measurements are buffered into memory of the peripheral device, but this may not be necessary in all examples. Therefore, the collector device's user interface may be used to output real time measurement data of a user or users.

Performance measurement system discussed herein may refer to a physiological performance measurement system for measuring physiological performance, such as physical activity, inactivity and/or sports training/exercise, performed by a user or a group of users.

FIG. 4 illustrates some embodiments. Referring to FIG. 4, peripheral devices 410 and 420 are shown together with a collector device 400. The collector device 400 may be configured to receive data streams from the peripheral devices. The data streams may be transmitted on a wireless radio connection, such as utilizing Bluetooth® and/or BLE technologies/standards. So, the data streams may be transmitted utilizing a data packet based technology where the peripheral devices 410, 420 obtain measurement samples, fit samples into data packet(s) and transmit these data packet(s) to the collector device 400. Hence, the transmission may not necessarily be a continuous stream of data, but a plurality of data packets transmitted on given or predetermined radio resources. The collector device 400 may obtain the data packets and obtain a data stream from the obtained data packets, wherein, for example, the data stream is a peripheral device specific. The transmission may be performed utilizing, for example, a device-to-device radio communication link (e.g. Bluetooth® or BLE link) which may be bidirectional or unidirectional. For example, if the communication link is a Bluetooth® link, the link may be bidirectional. In order to obtain the communication link, the peripheral device may need to be paired with the collector device 400. So, for example, both devices 410, 420 may be paired with the collector device 400. It is also possible, at least in some embodiments, the data stream(s) from the devices 410, 420 are broadcasted. Hence, the communication links and pairing are not necessary in all embodiments.

Referring to an embodiment of FIG. 4, the collector device 400 may broadcast the timing signal (block 432). This step may equal to step 202 of FIG. 2. The peripheral devices 410, 420 may detect the broadcasted timing signal respectively (block 434 and block 444).

The peripheral devices 410, 420 may input clock value into a data packet respectively (see block 436 and block 446). The clock value may refer to the clock value of the respective peripheral device 410, 420. The data packet may be a data packet that is to be transmitted to the collector device 400. In an embodiment, the data packet is the next to be transmitted data packet, i.e. the next data packet in queue for transmission. The clock value may refer to Real Time Clock (RTC) value. For example, the peripheral device 410, 420 may start/initiate its clock in response and/or upon starting/initiating measurement. In the known solutions, the clock value is not indicated to the collector device 400. In the present solution, the current clock value is added to the data packet. Current clock value may refer to the time instant at which the broadcasted timing signal is detected. Hence, both devices 410, 420 may obtain their current clock values substantially simultaneously, and add these values to the data packets. Therefore, the obtained current clock values may represent the same time instant and are comparable with each other. It is noted that the clock values may still be different due to, for example, different starting time of the measurement, different clock drifts, and/or different device configuration.

In blocks 438, 448, the peripheral devices 410, 420 transmit the data packets to the collector device. As shown in the Figure, the transmission windows may be timely consecutive. However, simultaneous transmission may be possible if frequency division or some other multi-transmission technique is utilized.

In block 450, the collector device 400 may synchronize the data streams based on the indicated clock values which are obtained from the data packets. It is noted that the data packets may further comprise the timing signal value which is detected by the peripheral device 410, 420 and added to the data packet. Hence, the syncing may be performed based on clock values that are indicated in response to the same broadcasted timing signal (e.g. block 432). It is further noted that the collector device 400 may take this into account when performing the syncing, i.e. that the clock values are indicated in response to the same or possibly different timing signals.

In an embodiment, the peripheral device 410, 420 continues measurement during and/or after including the clock value into the data packet (blocks 437, 447). So, before and after including the clock value into the data packet, the device 410, 420 may continue to include obtained samples into the same data packet. Hence, in an embodiment, the data packet comprises measurement samples. In an embodiment, the data packet comprises only the clock value (and possibly further the timing signal value as is explained later in more detail).

Similarly, after transmitting the data packet (blocks 438, 448), the device 410, 420 may continue to perform measurements and add obtained samples into next data packet (block 452, 454), and transmit said next data packet (block 456, 458). Clock value may not be added to these next data packets unless, for example, the collector device 400 indicates in a response message (or does not indicate positive reception of the clock value indicating data packet) that the clock value was not successfully received in response to broadcasting the timing signal (block 432). This may simply mean that the collector device 400 requests retransmission of the data packet. Also, if the collector device rebroadcasts the timing signal which is received by the peripheral device, the peripheral device may transmit the clock value similarly as in steps 434, 436, 438 and 444, 446, 448.

It is also noted that the proposed solution is not limited to two peripheral devices 410, 420. Only two devices are used in the examples due to simplicity and intelligibility reasons. Hence, there may be a plurality of peripheral devices configured to operate similar as devices 410, 420. Also, the collector device 400 may operate with more than two peripheral devices.

Figure 5A:
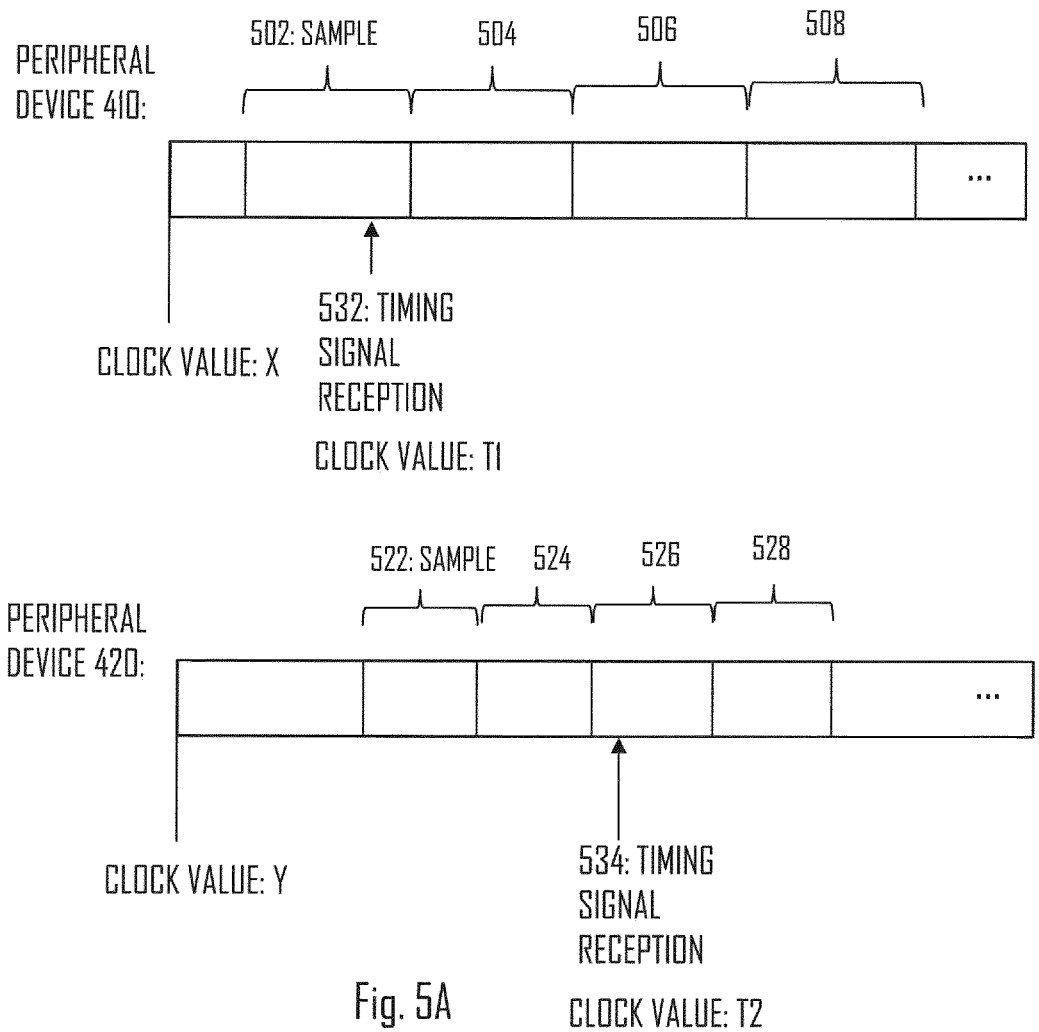
FIGS. 5A, 5B, 6A, 6B, 6C, 6D, 7A, and 7B illustrate some embodiments.
Figure 5B:
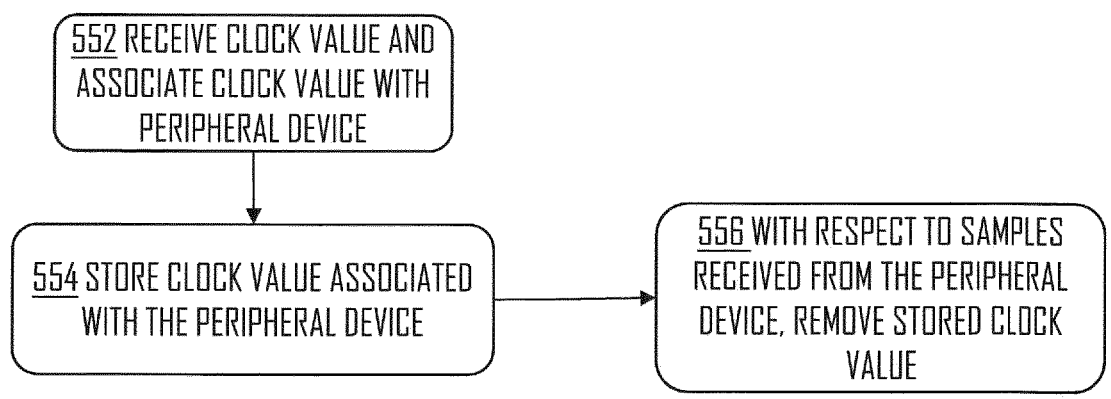

FIGS. 5A and 5B illustrate some embodiments. Generally, broadcasting may be performed on a plurality of channels. For example, there may be a certain number of different channels on which the broadcasting is performed in round robin style, i.e. consecutively one after another such that each broadcasting event comprises broadcasting on each channel (e.g. three channels). For example, BLE supports utilizing three different channels. In an embodiment, the broadcasting is performed on a single predetermined radio channel. E.g. on only one radio channel. This may be especially beneficial as now the peripheral devices 410, 420 may be configured to listen/detect the timing signal on only one channel (e.g. channel 37 in case of Bluetooth® broadcasting (e.g. BLE broadcasting)), thus providing a better chance to detect the broadcasted signal. So, the probability of the devices 410, 420 detecting the same timing signal may be increased which may further be beneficial in the synchronization (referred to also as syncing) process.

Referring to FIG. 5A, the peripheral devices 410, 420 are shown, wherein each device may obtain, by performing physiological measurements, physiological measurement samples 502, 504, 506, 508, 522, 524, 526, 528. Samples 502-508 may belong to device 410 and samples 522-528 may belong to device 420. These samples may be obtained and transmitted in the data packets to the collector device. In some embodiments, the data packets comprise raw measurement data. For example, the sensor device may directly transmit the obtained samples to the collector device 400. In some embodiments, the data packets comprise processed and/or preprocessed samples. For example, the sensor device may itself process the samples into one or more metric that is transmitted to the collector device 400.

As noted clock value at the start of the indicated sequences is X (i.e. device 410 clock value) and Y (i.e. device 420 clock value). It is noted that the sequences are not synchronized in the shown example. It is also noted that value X, Y does not necessarily indicate the start of the sequence, and may thus refer to some arbitrary moment during the measurement process. So, the collector device 400 may broadcast the timing signal at a certain time instant. The devices 410, 420 may detect the timing signal as indicated by arrows 532 and 534. Device 410 may store its clock value T1 into memory (e.g. directly to the next data packet) and device 420 may store its clock value T2 into memory (e.g. directly to the next data packet). T1 and T2 may represent clock values at the time of detecting the timing signal 532, 534. Thus, a reference point may be found, by the collector device 400, once T1 and T2 are received by the collector device.

Referring to FIG. 5B, in block 552, the collector device 400 receives a data packet from device 410, obtains T1 from the data packet and associates T1 with device 410. For example, association may mean associating T1 with identifier (e.g. unique identifier) of device 410. Similarly, the collector device 400 receives a data packet from device 420, obtains T2 from the data packet and associates T2 with device 420. In block 554, the collector device 400 may store the clock value T1, T2 into a memory, such as a database, application memory, or some other available memory. The storing may comprise storing the clock value T1, T2, and also clock values association with the device 410, 420. Hence, the collector device 400 may utilize stored clock values when samples from peripheral devices 410, 420 are received and processed. For example, this may mean that T1 is removed from all samples received from device 410 and T2 is removed from all samples received from device 420 (block 556). Removing here does not mean that the actual samples are removed somehow. It refers to changing time reference of the sample. Hence, if this removing is performed for all samples, the samples from different devices are synced timewise and thus are better comparable with each other. The removing may refer to moving the different samples (which may be biometric signals as function of time, such as heart rate as a function of time) based on the clock values such that the difference between clock values may be removed from the sample data. So, basically the removing refers to changing a time reference point in the respective sample data based on the clock value.

Basically, if clock value X is 0 and T1 is 198, and if clock value Y is 3000 and T1 is 3205, values 198 and 3205 may be used to synchronize the samples from devices 410, 420. Intelligent reader may notice that 198 is different than 3205. However, such difference may be caused by, for example, processing speed of the device 410, 420 or its communication circuitry, non-ideal radio environment and/or different distance between the device 410, 420 and the collector device 400. Again it is noted, the removing may mean that the clock value is used to change time reference point of the samples as will be understood by the skilled person. This is not possible in the known solutions as the clock value is not known by the collector device 400 or transmitted by the peripheral device 410, 420.

Figure 6A:
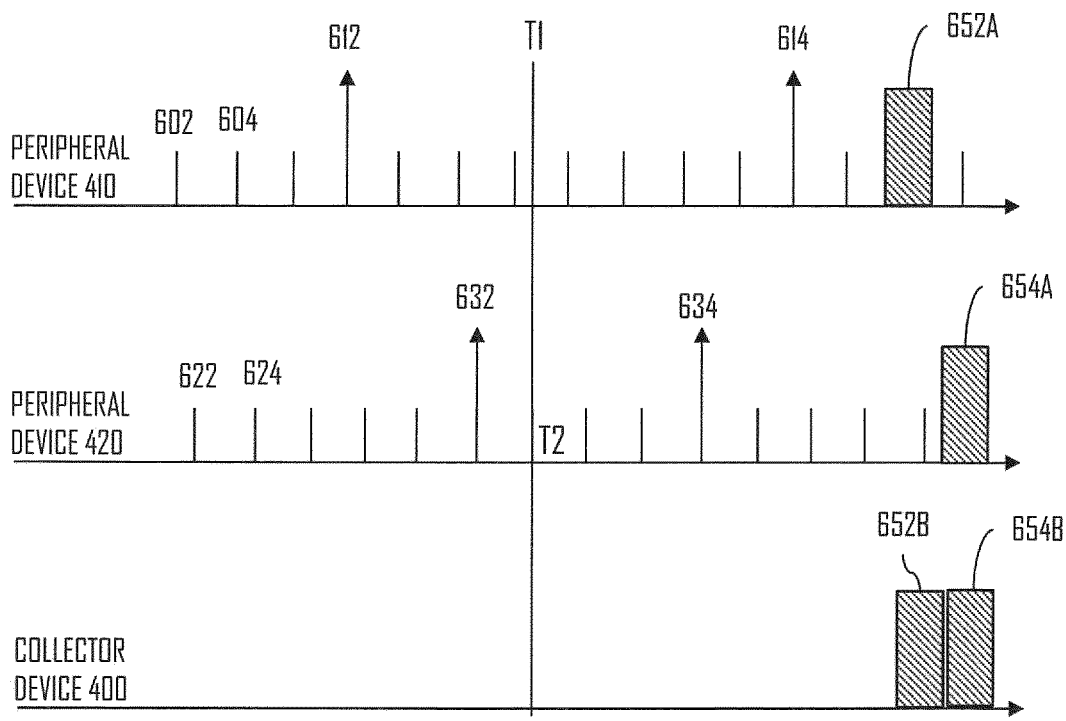
Figure 6B:
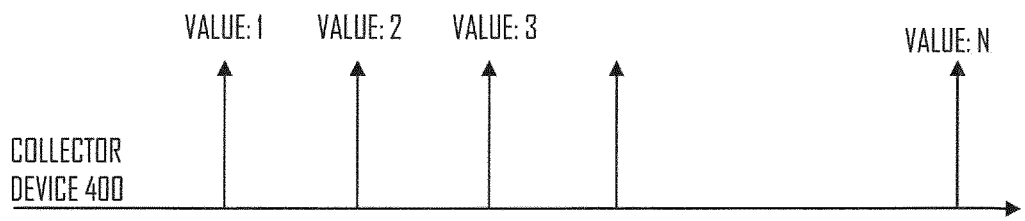

FIGS. 6A, 6B, 6C, and 6D illustrate some embodiments. Referring first to FIG. 6B, in an embodiment, the collector device 400 broadcasts a timing signal 642 with a certain interval.

In an embodiment, the timing signal is referred to as a time stamp or comprises a time stamp. In an embodiment, the timing signal indicates a value. The value may be, for example, an integer value, such as unsigned integer value. For example, the value may be 16 bit unsigned integer.

Figure 6C:
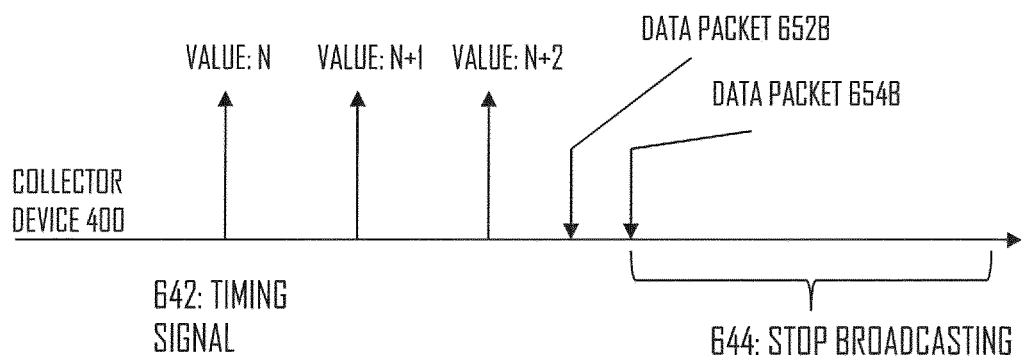

In an embodiment, as shown in FIG. 6B, the value of the timing signal 642 increases between each consecutive transmission (i.e. value=1, value=2, value=3, . . . value=N, wherein N denotes an integer value, such as unsigned integer value). Referring to FIG. 6C, this may be expressed as N, N+1, and N+2, wherein the value increases each time the timing signal is broadcasted. It is noted that the timing signal 642 may be transmitted with a constant interval. The collector device 400 may be configured to increase said timing signal value on each transmission. This may be beneficial as it is not likely that each peripheral device 410, 420 receives all timing signals (or advertising packets comprising the timing signal/timing signal value).

In an embodiment, it may suffice that each peripheral device 410, 420 detects at least one of the timing signals 642. In an embodiment, the peripheral device 410, 420 stops detection of timing signals upon detecting a timing signal 642.

In an embodiment, the collector device 400 stops broadcasting the timing signal 642 upon reception of clock values of each paired peripheral device 410, 420 (i.e. paired with the collector device 400).

In an embodiment, the data packet comprises a value of the received timing signal. That is, the peripheral device

410, 420 may further include value of the received timing signal into the data packet in addition to the clock value. Hence, the collector device 400 may determine the timing signal in response to which the clock value is received. Hence, for example, the syncing may be possible even if the clock values from different peripheral devices 410, 420 are received in response to different timing signals 642. However, at least in some examples it is not necessary to include the timing signal value into the data packet as the time interval between timing signals may configured such that the probability of mix-up is relatively low. Further, in an embodiment, if the clock values are received in response to the same broadcasted timing signal, there may be no need to include the timing signal value into the data packet. However, it may be beneficial to include the timing signal value into the data packet, by the device 410, 420, to further enhance the proposed solution. That is, this way the collector device 400 may determine, with greater accuracy, that the indicated clock values are related to/associated with the same timing signal value and/or same timing signal transmission.

Referring now to FIG. 6A, the transmission window, during/at which the data packet is transmitted, is the next possible transmission window 652A, 654A of the device 410, 420. So, for device 410 the next transmission window is window 652A after reception of the timing signal 642 at time instant corresponding to clock value T1. For device 420 the next transmission window is window 654A after reception of the timing signal 642 at time instant corresponding to clock value T2. In FIG. 6A the sample sequences are shown in a different way compared with FIG. 5A. However, this is simply due to illustration purposes. That is, FIG. 6A represents perhaps with greater accuracy that the timing signal 642, broadcasted by the collector device 400, is simultaneously detectable by both device 410, 420.

Referring still to FIG. 6A, clock of peripheral device 410 is illustrated with lines 602, 604 (others do not have reference signs) and clock of peripheral device 420 is illustrated with lines 622, 624 (others do not have reference signs). Arrows 612, 614, 632, 634 may represent samples, i.e. moments at which the device 410, 420 takes a measurement sample. It is possible, that if the timing signal 642 is received between clock beats (i.e. 602, 604), T1 value equals to the next possible clock beat as this may be the maximum time resolution (i.e. accuracy of the clock) of the device 410. Similar logic naturally applies to device 420, but in the example T2 seems to be exactly at clock beat.

So for example, the devices 410, 420 may gather samples 612, 614, 632, 634 into their next data packets due for transmission at transmission window 652A, 654B respectively. For example, the transmission windows 652A, 654A may be situated one after another, and received by the collector device 400 at corresponding reception slots 652B, 654B. That is, data packet transmitted at window 652A may be received at window 652B, and data packet transmitted at window 654A may be received at window 654B.

Referring to an embodiment of FIG. 6C, the peripheral device 410, 420 is configured to stop the detection of timing signals 642 upon detecting the timing signal broadcasted by the collector device 400. That is, once the reference point is established there may be no need to continue detection on the broadcast channel(s) to save energy.

However, in another embodiment, the peripheral device 410, 420 continues detection on the broadcast channel(s), and reports its clock value if further timing signals are received. That is, it may be beneficial to resynchronize the data streams, for example, after a certain time has passed from the previous synchronisation.

In an embodiment, the peripheral device 410, 420 initiates the detection of timing signals 642 as a response to initiating the performing the physiological measurements. So, for example, when user starts measurement using a sensor, the sensor may be configured to initiate the timing signal detection.

As mentioned above, in an embodiment, the collector device 400 stops broadcasting the timing signal 642 upon reception of clock values of paired peripheral device 410, 420 (i.e. paired with the collector device 400). This is shown with reference number 644 in FIG. 6C. This may mean that the broadcasting is stopped if clock value of each of the paired peripheral devices 410, 420 is received. In an embodiment, the broadcasting is stopped if clock value of each paired device 410, 420 is received in response to the same broadcasted message. Otherwise, the broadcasting may continue, for example. When the broadcasting is stopped, the peripheral devices may continue measuring the physiological data and transmitting the data packets containing the physiological measurement data and time stamps indicating the (measurement) timing of the physiological measurement data. Accordingly, such data packets may be void of any clock value related to the broadcast message. In other words, a peripheral device may transmit the data packet containing the clock value between data packets containing no such clock value.

Figure 6D:
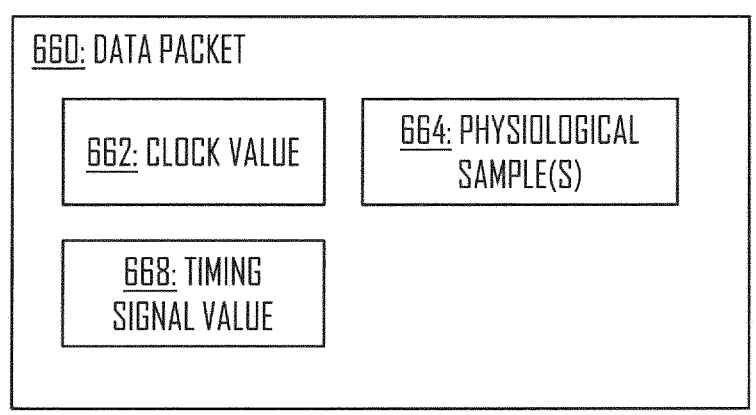

Referring to FIG. 6D, a data packet 660 is shown according to some embodiments. As indicated above, the data packet 660, transmitted from a peripheral device to the collector device 400, may comprise a clock value 662 indicating the current clock (e.g. RTC) value of the peripheral device at the moment when the timing signal 642 is received. Additionally, in an embodiment, the data packet 660 may comprise the timing signal value 668. Additionally, in an embodiment, the data packet 660 may be comprise one or more physiological measurement samples 664 acquired by the peripheral device performing the physiological measurement.

Figure 7A:
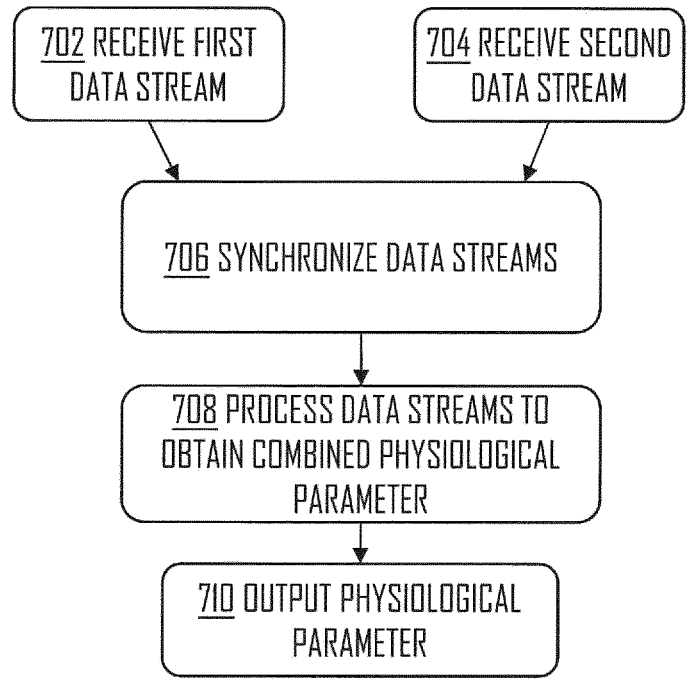
Figure 7B:
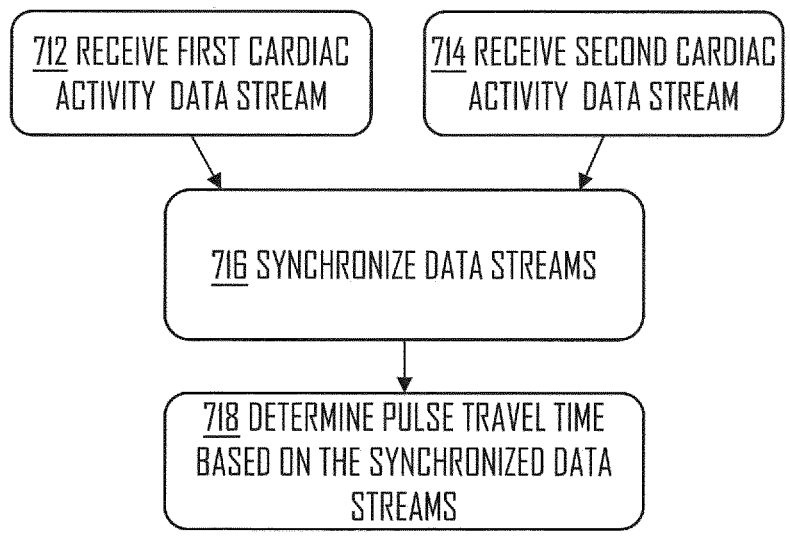

FIGS. 7A and 7B illustrate flow diagrams according to some embodiments. Referring to FIG. 7A, the collector device 400 may be configured to perform operations comprising: receiving (block 702) a first data stream from a first peripheral device associated with a user; receiving (block 704) a second data stream from a second peripheral device associated with the user; synchronizing (block 706) the first and second data streams based on the received data packets indicating clock values of the first and second peripheral devices respectively; processing (block 708) the first and second data streams to obtain a physiological parameter derivable from the combination of the first and second data streams; and outputting (block 710) the physiological parameter.

The outputting of block 710 may comprise transmitting the physiological parameter to an external device, storing the parameter, displaying the parameter on a display, and/or providing a haptic and/or visual output based on the parameter, to name a few examples.

In the example, of FIG. 7A the data streams are obtained with respect to the same user. However, as noted above, it is also possible to receive data streams from multiple peripheral devices associated with different users, or that at least one peripheral device is associated with a different user.

There are different use cases for utilizing the synchronized data streams. For example, the use cases may include, but are not necessarily limited to:

Blood pressure calculation: Combining ECG and PPG data for obtaining pulse transit time (PTT) and/or pulse wave velocity (PWV). ECG data and PPG data may be measured by different peripheral devices. The collector device may use the time stamps indicating the (measurement) timing of the measurement data to combine the ECG data with PPG data that both relate to detection of the same blood pulse, thus enabling computation of the PTT and/or PWV. For example, after synchronizing the peripheral devices to the common time reference the collector device may combine ECG data with PPG data that has a time stamp value closest to a time stamp value of the ECG data, but after the time stamp value of the ECG data. The ECG data indicates detection of a blood pulse at a heart while the PPG data indicates detection of the block pulse at another body part, e.g. at a hand. Therefore, The PPG detection occurs after the ECG detection.

Stroke volume calculation: Combining ECG and bioimpedance data from separate sources for obtaining stroke volume.

Running power calculation: combine data from several sensors. For example, speed and altitude data can be used to calculate running power. In a more elaborate solution, running power can be calculated from force (or pressure) and speed measurements (force may be measured from insoles, acceleration from footpods). Data streams may be synchronized to the common time reference and combined to obtain running power metric, e.g. by using the time stamps.

Technique analysis: combining data from multiple motion sensors for motion analysis (swimming, running, and practically any sport).

Real time performance indices: Running, skiing, or cycling power in relation to effort, the latter measured for example by heart rate or cardiac output.

Referring to FIG. 7B illustrating an example embodiment, in blocks 712, 714 the collector device 400 receives a first cardiac activity data stream and a second cardiac activity data stream. The data streams are synced in block 716. Further, the collector device 400 may determine a pulse transit time based on the synchronized first and second cardiac activity data streams (block 718). So, FIG. 7B illustrates a further embodiment of FIG. 7A.

Figure 7C:
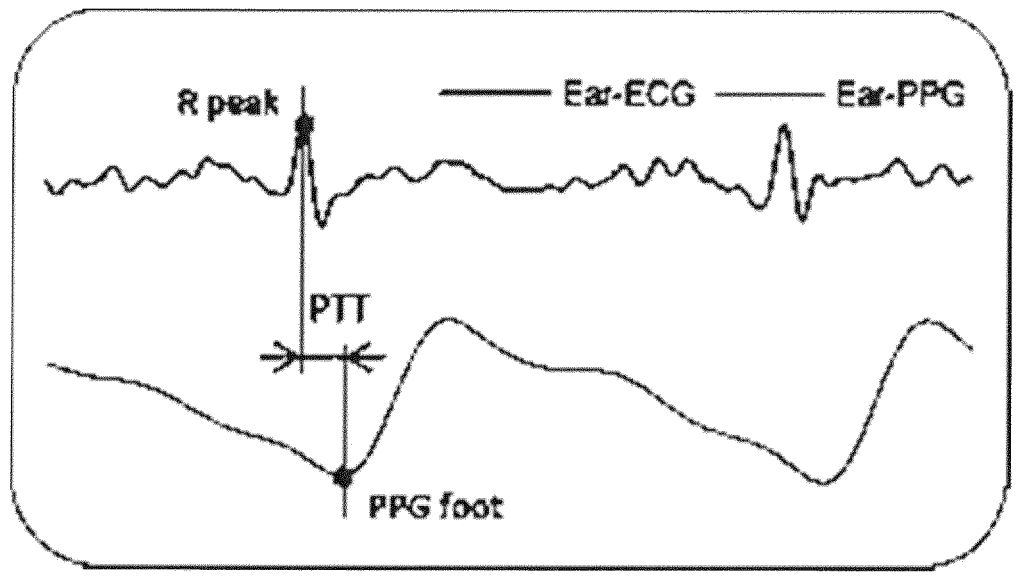
FIG. 7C illustrates an example embodiment of pulse transit time determination.

FIG. 7C illustrates a specific example of how PTT can be measured from two different cardiac activity data streams. As shown, PTT may denote delay or time between R peak value, obtained from ECG sensor (e.g. ear-ECG, or chest ECG) and PPG foot value, obtained from PPG sensor (e.g. ear-PPG, wrist unit optical sensor, or arm sensor). As these two different data streams are synchronized as proposed by solution herein, the PTT may be calculated with even more accuracy. PTT signal or value may further be used to determine PWV, stress status, sleep status, and/or recovery status. Hence, for example, the more accurate PTT may be handy in determining the amount of training (i.e. not too much, but not too little). It is also noted that from PWV, blood pressure may be calculated based on determined/set distance between the two measurement locations (i.e. the distance the blood pulse needs to travel between the ECG and PPG measurement areas). Another example of used sensors may be the wrist or arm PPG in combination with a weight scale Ballistocardiogram (BCG). It is noted that virtually any combination of different cardiac activity sensor may be used as long as a delay between different cardiac activity events may be detected from multiple locations on the user. As said, data streams from these different sensors may be synced utilizing the broadcasted timing signal which causes the sensors to indicate their current clock value (e.g. RTC value).

As noted above, there are other examples of how to utilize the synced data streams, such as stroke volume calculation, running power calculation, and/or motion analysis.

Regarding stroke volume calculation, referring to FIG. 7A, in blocks 702, 704 the collector device 400 may receive ECG data and bioimpedance data. These data streams may be synchronized. ECG data may be measured using an ECG sensor, and bioimpedance may be measured using a bioimpedance sensor. Patent publication US 2002/0193689 discloses one method of computing the stroke volume by using the bioimpedance and the ECG, and the collector device 400 may employ such a method in some embodiments.

Regarding running power calculation, referring to FIG. 7A, in blocks 702, 704 the collector device 400 may receive speed data and altitude data from different peripheral devices. These data streams may be synchronized to the common time reference. Running power may be calculated based on, for example, speed data and altitude data. That is, the running power calculation method may comprise: obtaining speed data and angle data (directly or by calculating route angle based at least on the altitude data) on a route of the user; obtaining an energy consumption estimation for a predetermined distance at least on the basis of a predetermined model and the angle data; and obtaining the running power data at least on the basis of the energy consumption estimation and the speed data. The running power data may indicate a running power estimation of the user.

Regarding motion analysis, referring to FIG. 7A, in blocks 702, 704 the collector device 400 may receive motion data streams from a plurality of different motion sensors. These data streams may be synchronized to the common time reference and combined by using the time stamps. Based on these synced data streams, motion analysis may be performed and may include gesture detection and/or posture detection (e.g. running posture) to name a few examples. Motion analysis may reveal faults or errors in technique, such as too long or too short step during running. Other examples may be performing motion analysis for golf strike or some other sports which involves rackets, bats, clubs, mallets, or sticks.

So the physiological parameter obtained in block 708 and outputted in block 710 may refer to and/or comprise motion analysis, running power, stroke volume, PTT, PWV and/or blood pressure to name a few examples. Other examples may include training load, running index and energy consumption. The benefit may be that using the provided synchronizing method, the different physiological parameters may even better describe the performed physical activity. This may benefit coaching activities and/or development of user (can be referred to as a trainee or exerciser).

It is noted that the collector device 400 may perform the steps of FIGS. 7A and 7B.

Figure 8A:
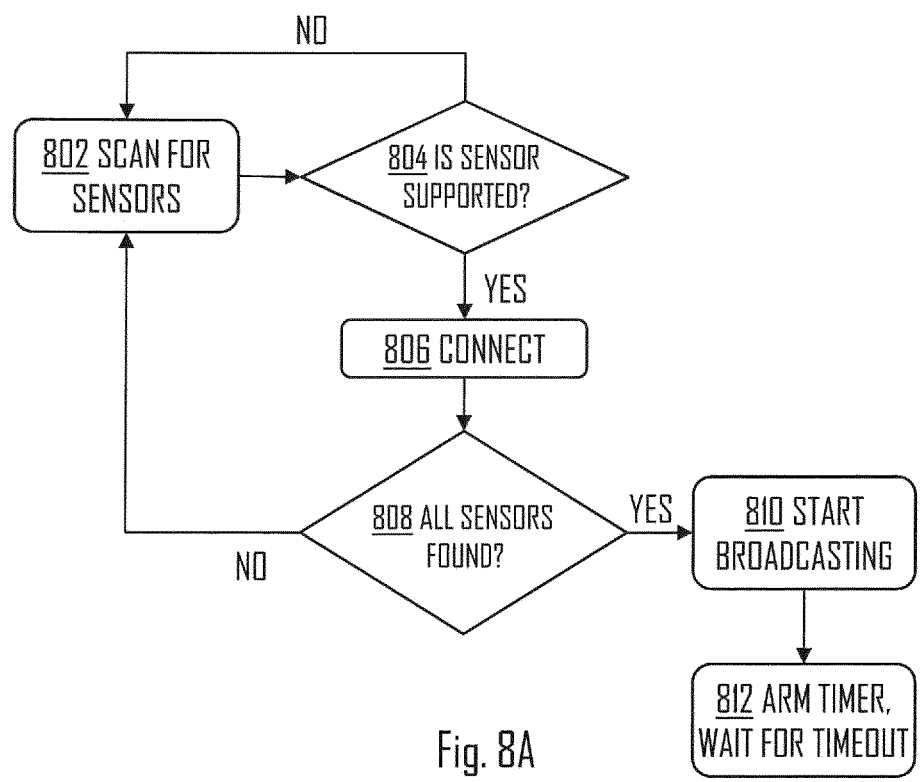
FIGS. 8A and 8B illustrate flow diagrams according to some embodiments.
Figure 8B:
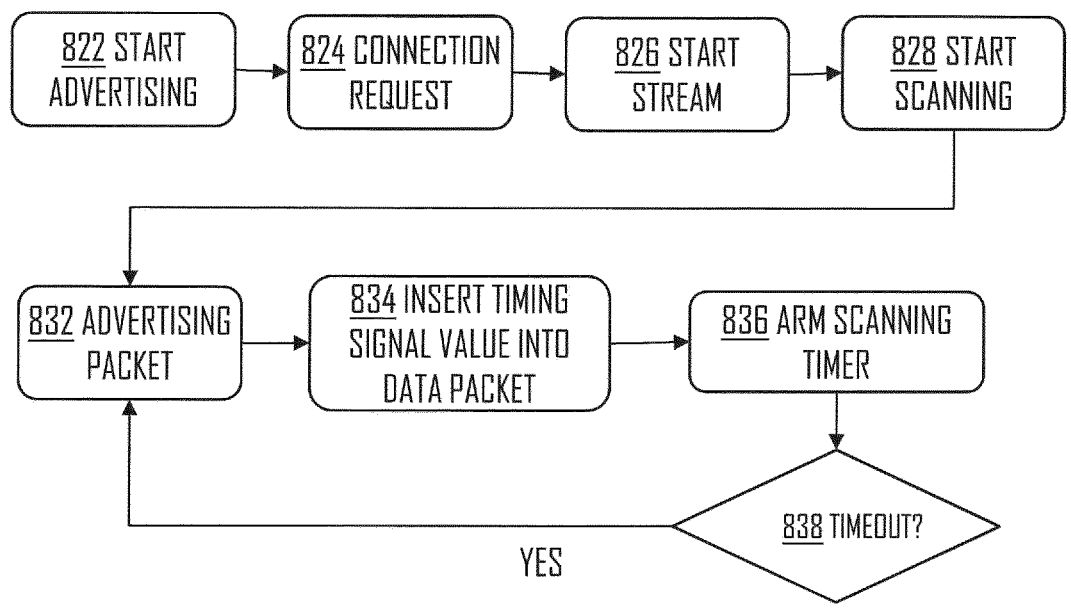

FIGS. 8A and 8B illustrate some example embodiments. Referring to FIG. 8A, in block 802, the collector device 400 may scan for sensors (i.e. peripheral devices which may be sensors). If sensor is found, in block 804 the collector device 400 may determine whether or not the sensor is supported. If not, the process goes back to block 802. If yes, the process continues to block 806 in which the sensor and the collector device are communicatively connected (e.g. radio link) with each other.

The process then continues to block 808. If all sensors are found (e.g. based on timer and/or based on detecting all sensors), the process may continue to block 810. If not, the process may proceed again to block 802.

In block 810, once all sensors are found/upon finding all sensors, the collector device 400 may initiate broadcasting the timing signal as in block 202, for example.

In block 812, which is optional, the collector device 400 arms a timer and waits for the timer to expire. If the timer expires and/or in response to timer expiring, the collector device increments the timing signal value (can be referred to as time stamp) and continues the broadcasting with the incremented value. The value may be incremented on each timeout (see e.g. FIG. 6B and timing signal values 1, 2, 3, ... N).

Referring to FIG. 8B, a peripheral device, such as device 410 or 420, may start advertising (block 822). For example, the advertising may be started after and/or in response to powering up the peripheral device.

In block 824, connection request may be transmitted between the collector device 400 and the peripheral device. It may be up to configuration which device initiates the communication link, but for example, the peripheral device may broadcast its identifier and the collector device 400 may request connection.

In block 826, the peripheral device may initiate data stream transmission via the communication link to the collector device 400. That is, measurement samples may be transmitted to the collector device 400.

In block 828, the peripheral device may start scanning for broadcasted messages from the collector device 400. The scanning may also be referred to as advertising. For example, the peripheral device may be configured to utilize white list or a black list such that it detects only broadcasted messages from the collector device 400 (e.g. based on identifier of the collector device 400 acquired during establishment of the communication link (e.g. block 824)). The scanning may be initiated in response to starting the peripheral device or initiating measurement or data transmissions. It is further possible that the collector device 400 configures the broadcasting channel and/or requests the peripheral device to start detecting the broadcasted messages via the established communication link between the device 400 and the peripheral device.

In block 832, the peripheral device detects/receives an advertising packet. The peripheral device may, in block 834, add clock value into the next data packet based on the received advertising packet. In an embodiment, the timing signal value (which may be a time stamp, for example) is also added into the data packet. The peripheral device may acquire the timing signal value by parsing the timing signal (which may be an advertising packet), for example.

In an embodiment, the peripheral device arms scanning timer in block 836. The peripheral device may not detect/listen broadcasted messages on given frequency before the timer expires. If the timer expires (block 838), the process may continue to block 832 (or block 828) in which the peripheral device may again start to scan for broadcasted messages, and possibly detect an advertising packet (i.e. a broadcasted message).

The collector device 400 may receive the data packets from the different peripheral devices 410, 420. The collector device 400 may then detect same timing signal value (e.g. time stamp) from the data packets. The timing signal value sets a reference point for indicated clock values. Thus, the collector device 400 may, with a greater certainty, determine that the clock values from devices 410, 420 are associated with the same timing signal (and more particularly with the same timing signal transmission event) as both clock values are indicated with the same timing signal value. For example, the peripheral device 410 may indicate clock value 198 associated with timing signal value 3, and the peripheral device 420 may indicate clock value 3205 associated with timing signal value 3. Hence, the collector device 400 may determine that both clock values are associated with the same timing signal value and thus the synchronization may be performed based on the indicated clock values (e.g. RTC value) 198 and 3205.

In an embodiment, the data packet (e.g. transmitted in block 306, 438, 448, 456, and/or 458) comprises a data structure. In an embodiment, the data structure may have the following format:

| Header | Payload Data | CRC |
|--------|--------------|-----|

The header may comprise control or management information needed to deliver the payload data, the payload data may comprise measurement data (e.g. measurement samples), clock value (e.g. RTC clock value) and timing signal value according to any one of the above-described embodiments. Further, the payload data may comprise a ring counter. A cyclic redundancy check (CRC) part may comprise CRC bits for error detection and/or correction.

In an embodiment the header may have the following format:

| Pad | Preamble | Sync | Tx index | Type | Len | SensorID | Timestamp |
|-----|----------|------|----------|------|-----|----------|-----------|

Pad field may comprise padding bits that have no specific use, preamble and synchronization sequence (Sync) may comprise bits needed for detecting the data structure in a receiver and to synchronize to the header. A transmission index (Tx index) may indicate a position of the payload data in a series of data packets, and it may be used for reordering data packets and finding lost data packets. Reason field may indicate a type of the data structure. The Type field or another field of the header may comprise a value indicating what type of payload data the data portion carries. One value may be reserved for clock value to indicate that the payload data carries the clock value of the peripheral device. For example, the collector device receiving the data packet may determine, based on said one value, that the payload data of the received data packet carries the clock value of the peripheral device. Length field (Len) specifies the total length of the data structure, SensorID field carries an identifier of an entity that provides the data, e.g. peripheral device identifier. Timestamp field may be used for a timestamp indicating the timing of the data comprised in the payload part of the data structure. However, this may be different timestamp than the broadcasted timestamp (i.e. by the collector device 400) and further different than the clock value indicated in the payload data part.

In an embodiment, the data structure is a frame such as a radio frame.

In an embodiment, the data structure is a Bluetooth® (e.g. BLE) data structure and the data packet is a Bluetooth® (e.g. BLE) data packet.

Figure 9:
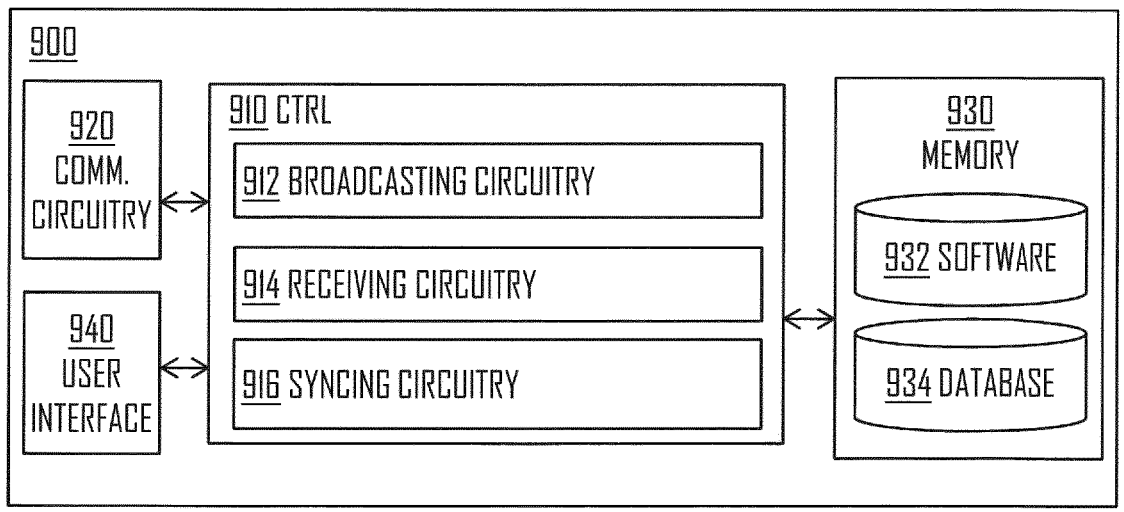
FIGS. 9 and 10 illustrate apparatuses according to some embodiments.
Figure 10:
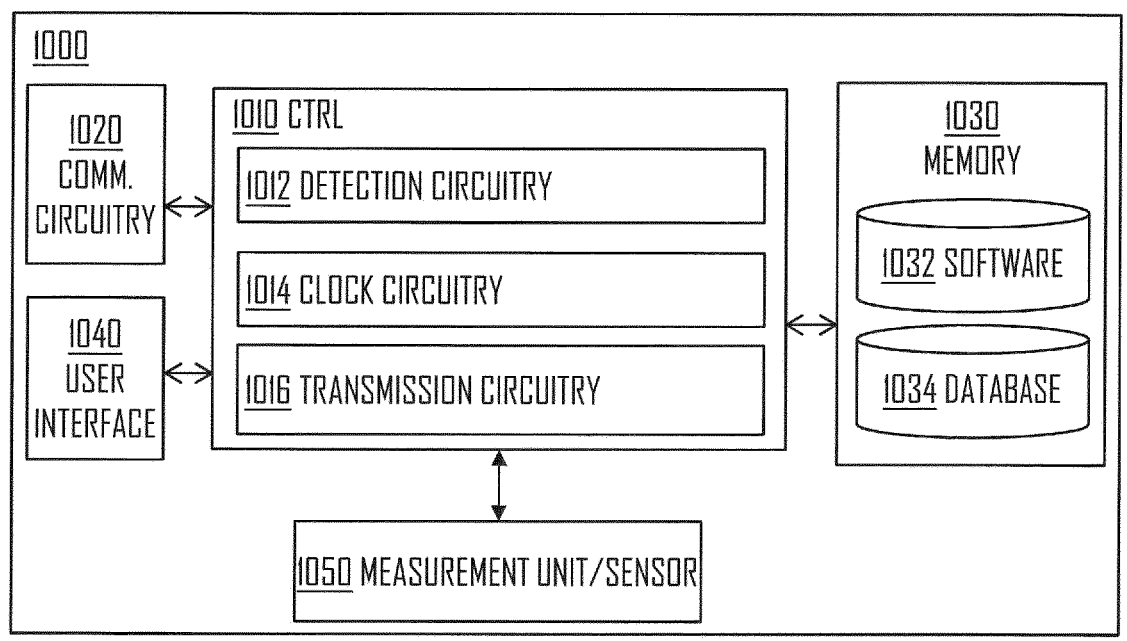

FIGS. 9 and 10 show block diagrams of apparatuses according to some example embodiments. Referring to FIGS. 9 and 10, apparatuses 900, 1000 comprise a control circuitry (CTRL) 910, 1010, such as at least one processor, and at least one memory 930, 1030 including a computer program code (software) 932, 1032, wherein the at least one memory and the computer program code (software) 932, 1032, are configured, with the at least one processor, to cause the respective apparatus 900, 1000 to carry out any one of the embodiments described above, such as with reference to FIGS. 1 to 8B, or operations thereof.

Referring to FIGS. 9 and 10, the memory 930, 1030 may be implemented using any suitable data storage technology, such as semiconductor based memory devices, flash memory, magnetic memory devices and systems, optical memory devices and systems, fixed memory and removable memory. The memory 930, 1030 may comprise a database 934, 1034 for storing data. Data may comprise, for example, clock value(s) and/or timing signal value(s). For example, the clock value associated with a peripheral device may be stored into said database. The database may be internal and/or external to the apparatus.

The apparatus 900, 1000 may further comprise communication circuitry 920, 1020 (e.g. wireless communication circuitry) comprising hardware and/or software for realizing communication connectivity according to one or more communication protocols, such as Bluetooth® or BLE. The communication circuitry may comprise standard well-known components such as an amplifier, filter, frequency-converter, (de)modulator, and encoder/decoder circuitries and one or more antennas.

The apparatus 900, 1000 may also comprise user interface 940, 1040 comprising, for example, at least one keypad, a microphone, a touch display, a display, a speaker, etc. The user interface 940, 1040 may be used to control the respective apparatus by a user of the apparatus 900, 1000. For example, the user interface may be used to output the physiological parameter acquired from the synchronized data streams.

In an embodiment, the apparatus 900 may be or be comprised in a collector device, such as the collector device 400.

According to an embodiment, the CTRL 910 comprises a broadcasting circuitry 912 configured to perform at least operations described with respect to block 202; a receiving circuitry 914 configured to perform at least operations described with respect to block 204; and a syncing circuitry 916 configured to perform at least operations described with respect to block 206.

In an embodiment, the apparatus 1000 may be or be comprised in a peripheral device, such as the peripheral device 410 and/or 420.

According to an embodiment, the CTRL 1010 comprises a detection circuitry 1012 configured to perform at least operations described with respect to block 302; a clock circuitry 1014 configured to perform at least operations described with respect to block 304; and a transmission circuitry 1016 configured to perform at least operations described with respect to block 306.

Further, the apparatus 1000 may comprise one or more measurement unit or sensor 1050 configured to perform the physiological measurement. Different examples of such sensors are given above, but may include at least: cardiac activity circuitry (e.g. PPG sensor and/or ECG sensor), motion circuitry (e.g. gyroscope and/or accelerometer), satellite positioning circuitry (e.g. GPS), force sensor, and/or pressure sensor. thus, the apparatus 1000 may be, for example, a chest strap device, wrist device, food pod, shoe insole apparatus, bike computer, ski pole apparatus (i.e. integrated with a ski pole), or some other sensing device configured to operate according to the proposed solution.

In an embodiment, there is provided a collector device 400 of a performance measurement system, the collector device 400 comprising means for causing the collector device 400 to perform the functionalities/steps of the collector device 400 as described above. The means may comprise, for example, the CTRL 910 and its different implementations.

In an embodiment, there is provided a peripheral device 410, 420 of a performance measurement system, the peripheral device 410, 420 comprising means for causing the peripheral device at least to perform the functionalities/steps of the peripheral device 410, 420 as described above. The means may comprise, for example, the CTRL 1010 and its different implementations.

According to an aspect there is provide a system comprising the collector device 400 and a plurality of peripheral devices 410, 420.

According to an aspect there is provided a computer readable medium comprising program instructions for causing an apparatus at least to perform the method as described herein. For example, this may include performing the steps of the collector device 400 and/or peripheral device 410, 420.

So, in summary a collector device 400 may be configured to perform advertising on a broadcast channel(s) (e.g. Bluetooth®, such as BLE). The advertising may comprise broadcasting an advertising packet comprising a timing signal. Further, a plurality of peripheral devices 410, 420 may be configured to perform passive scanning of advertising packets on the broadcast channel. The peripheral devices 410, 420 may detect said timing signal and in response to detecting obtain their internal clock value (or sensor clock value), e.g. RTC value, and insert said clock value into a next data packet that is to be transmitted to the collector device 400 on an established radio communication link between the respective peripheral device and the collector device. The radio communication link may utilize, for example, the same radio technique (e.g. Bluetooth®, such as BLE), and may be established earlier for transmitting the measurement data to the collector device. The data packet may further comprise measurement data obtained by the peripheral device. It may be possible that there is no radio communication link and that the peripheral devices also broadcast their data packets including the measurement data and/or the clock value. The collector device 400 may obtain the clock values, and perform, based on the obtained clock values, data stream synchronization on the data streams obtained from the peripheral device.

In an embodiment, block 306 comprises wireless broadcasting of the data packet (e.g. according to Bluetooth®, such as BLE standards).

In an embodiment, block 306 comprises transmission on an established device-to-device wireless radio communication link (e.g. Bluetooth®, such as BLE) between the peripheral device and the collector device.

According to an embodiment, the Bluetooth® may be replaced by using some other close range wireless radio protocol. Hence, reference regarding broadcasting and transmitting may be made generally to close range wireless radio protocols.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with FIGS. 1 to 8B may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of FIGS. 1 to 8B or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of FIGS. 1 to 8B, or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 1 to 8B may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A method in a collector device of a physiological performance measurement system, the method comprising:
   broadcasting a timing signal on a predetermined radio channel;
   receiving a data packet from each of a plurality of peripheral devices configured to perform measurements with respect to one or more users and to transmit physiological measurement data on the one or more users to the collector device, wherein the data packet indicates a clock value of a respective peripheral device, the clock value indicating a time instant at which the broadcasted timing signal has been detected by the respective peripheral device, and wherein the data packet further comprises a time stamp indicating timing of the physiological measurement data; and
   synchronizing data streams from the plurality of peripheral devices with each other based on the indicated clock values.

2. The method of claim 1, wherein the broadcasting is performed only on one predetermined radio channel.

3. The method of claim 1, wherein the collector device synchronizes the plurality of peripheral devices to a same time reference by using the clock values.

4. The method of claim 3, wherein the collector device combines, by using the time stamps, the physiological measurement data acquired from the plurality of peripheral devices.

5. The method of claim 4, further comprising:
   receiving a first data stream from a first peripheral device associated with a user;
   receiving a second data stream from a second peripheral device associated with the user;
   synchronizing the first and second data streams based on the received data packets indicating clock values of the first and second peripheral devices respectively;

processing the first and second data streams to obtain a physiological parameter derivable from the combination of the first and second data streams; and outputting the physiological parameter.

6. The method of claim 5, wherein the first data stream comprises cardiac activity data obtained from a first measurement area and the second data stream comprises cardiac activity data obtained from a second measurement area, the method further comprising:

determining a pulse transit time based on the synchronized first and second data streams.

7. A peripheral device of a physiological performance measurement system, the peripheral device comprising:

a control circuitry; and a wireless communication circuitry, wherein the control circuitry is configured, together with the wireless communication circuitry, to perform measurements with respect to a user and to transmit physiological measurement data on the user to a collector device, and to perform operations comprising:

initiating detection of timing signals on a predetermined radio channel;

in response to detecting a timing signal broadcasted by the collector device, including an information element, indicative of a clock value of the peripheral device at a time instant at which the broadcasted timing signal has been detected by the peripheral device, into a data packet to be transmitted during a transmission window; and transmitting the data packet to the collector device during the transmission window, the data packet comprising the physiological measurement data and a time stamp indicating timing of the physiological measurement data.

8. The method of claim 1, wherein the collector device receives said data packet between data packets containing no such clock value.

9. A method in a peripheral device of a physiological performance measurement system, the method comprising:

initiating detection of timing signals on a predetermined radio channel, wherein the peripheral device is configured to perform measurements with respect to a user and to transmit physiological measurement data on the user to a collector device;

in response to detecting a timing signal broadcasted by the collector device, including an information element, indicative of a clock value of the peripheral device at a time instant at which the broadcasted timing signal has been detected by the peripheral device, into a data packet to be transmitted during a transmission window; and transmitting the data packet to the collector device during the transmission window, the data packet comprising the physiological measurement data and a time stamp indicating timing of the physiological measurement data.

10. The method of claim 9, further comprising:

listening for the broadcasted timing signal only on one predetermined radio channel.

11. The method of claim 9, wherein the transmission window is a next possible transmission window.

12. The method of claim 9, further comprising:

including a value of the received timing signal into the data packet.

13. The method of claim 9, further comprising:

initiating the detection of timing signals as a response to initiating the performing the physiological measurements; and stopping the detection of timing signals upon detecting the timing signal broadcasted by the collector device.

14. The method of claim 9, wherein the peripheral device transmits said data packet between data packets containing no such clock value.

15. A collector device of a physiological performance measurement system, the collector device comprising:

a control circuitry; and a wireless communication circuitry, wherein the control circuitry is configured, together with the wireless communication circuitry, to perform operations comprising:

broadcasting a timing signal on a predetermined radio channel;

receiving a data packet from each of a plurality of peripheral devices configured to perform measurements with respect to one or more users and to transmit physiological measurement data on the one or more users to the collector device, wherein the data packet indicates a clock value of a respective peripheral device, the clock value indicating a time instant at which the broadcasted timing signal has been detected by the respective peripheral device, and wherein the data packet further comprises a time stamp indicating timing of the physiological measurement data; and synchronizing data streams from the plurality of peripheral devices with each other based on the indicated clock values.

16. The collector device of claim 15, wherein the control circuitry is configured, together with the wireless communication circuitry, to perform the broadcasting only on one predetermined radio channel.

17. The collector device of claim 15, wherein the control circuitry is configured, together with the wireless communication circuitry, to synchronize the plurality of peripheral devices to a same time reference by using the clock values.

18. The collector device of claim 17, wherein the control circuitry is configured, together with the wireless communication circuitry, to combine, by using the time stamps, the physiological measurement data acquired from the plurality of peripheral devices.

19. The collector device of claim 18, wherein the control circuitry is configured, together with the wireless communication circuitry, to perform operations comprising:

receiving a first data stream from a first peripheral device associated with a user;

receiving a second data stream from a second peripheral device associated with the user;

synchronizing the first and second data streams based on the received data packets indicating clock values of the first and second peripheral devices respectively;

processing the first and second data streams to obtain a physiological parameter derivable from the combination of the first and second data streams; and outputting the physiological parameter.

20. The peripheral device of claim 7, wherein the control circuitry is configured, together with the wireless communication circuitry, to include a value of the received timing signal into the data packet.

* * * * *